United States Patent
Venturini

(10) Patent No.: US 6,699,251 B1
(45) Date of Patent: Mar. 2, 2004

(54) BONE SCREW FOR EXTERNAL FIXATORS

(75) Inventor: Daniele Venturini, Povegliano Veronese (IT)

(73) Assignee: Orthofix S.R.L., Milan (IT)

( * ) Notice: Subject to any disclaimer, the term of this patent is extended or adjusted under 35 U.S.C. 154(b) by 0 days.

(21) Appl. No.: 09/937,950
(22) PCT Filed: Apr. 3, 2000
(86) PCT No.: PCT/EP00/02952
§ 371 (c)(1), (2), (4) Date: Nov. 30, 2001
(87) PCT Pub. No.: WO00/61021
PCT Pub. Date: Oct. 19, 2000

(30) Foreign Application Priority Data

Apr. 8, 1999 (EP) .............................................. 99830203

(51) Int. Cl.⁷ ............................................... A61B 17/84
(52) U.S. Cl. ........................................................ 606/73
(58) Field of Search ............................. 606/72, 73, 65, 606/66; 411/2, 5, 402, 411, 424

(56) References Cited

U.S. PATENT DOCUMENTS

| | | | | |
|---|---|---|---|---|
| 411,000 A | * | 9/1889 | Anderson | ................... 411/402 |
| 3,370,341 A | * | 2/1968 | Allsop | ......................... 29/413 |
| 3,915,162 A | | 10/1975 | Miller | |
| 4,492,500 A | * | 1/1985 | Ewing | ............................ 411/5 |
| 4,790,297 A | | 12/1988 | Luque | |
| 5,112,331 A | | 5/1992 | Miletich | |
| 5,653,710 A | * | 8/1997 | Harle | ........................... 606/73 |
| 6,090,110 A | * | 7/2000 | Metz-Stavenhagen | ........ 606/61 |
| 6,193,719 B1 | * | 2/2001 | Gournay et al. | ............... 606/61 |

* cited by examiner

Primary Examiner—Kevin Shaver
Assistant Examiner—Michael B. Priddy
(74) Attorney, Agent, or Firm—Leydig Voit & Mayer, Ltd.

(57) ABSTRACT

The invention relates to a bone screw for use with external bone fracture fixation devices, comprising a substantially cylindrical shank (2) with a longitudinal axis (X-X), a head (3) formed at a free end (4) of the shank (2) and having substantially the same thickness as the shank (2), and a threaded portion (5) terminated with a tip (6) at the opposite end from the free end (4). Advantageously, the screw head (3) includes a first flat (7) extending parallel to the longitudinal axis (X-X) from the free end (4), at least a second flat (8) aligned to the first flat (7) at a predetermined spacing therefrom, and at least a non-flat spacer portion (9) provided between the flats (7, 8). The spacer portion (9) is arranged to enable said shank (2) to be cut off if necessary, and is formed with a groove (11) of predetermined depth to define a location of potential cut off of the shank (2).

6 Claims, 1 Drawing Sheet

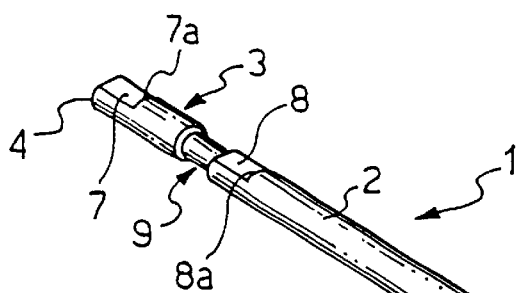
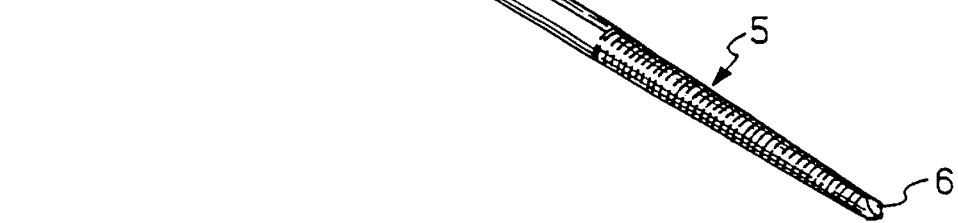
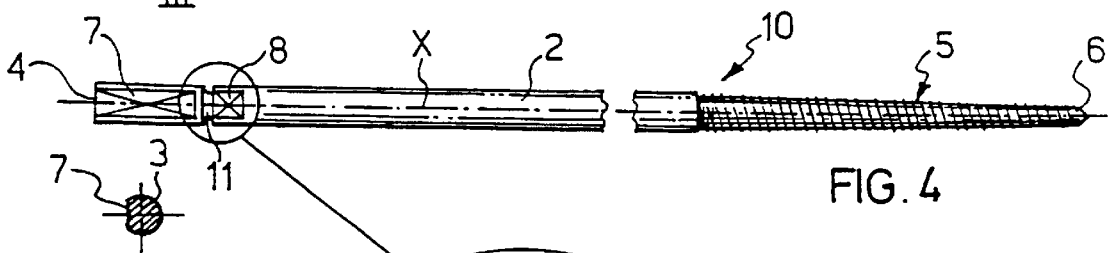
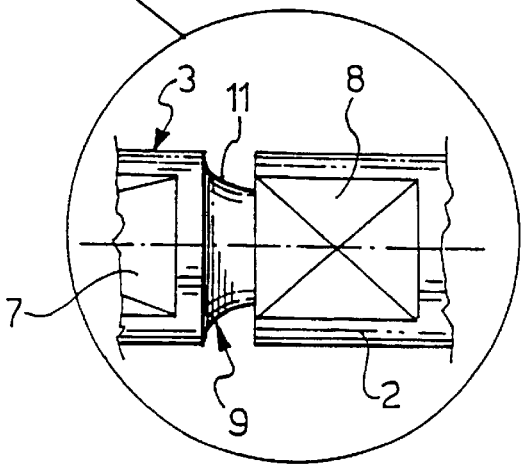

BONE SCREW FOR EXTERNAL FIXATORS

DESCRIPTION

1. Field of the Invention

This invention broadly relates to external fixation devices for reducing bone fractures.

More particularly, the invention relates to a bone screw for use to secure external bone fracture fixation devices.

2. Prior Art

As is well known, a widely adopted method of reducing bone fractures is based nowadays on the use of so-called external fixation devices which allow fractures to be consolidated in highly critical areas, as may be especially those proximate to joints, or fractures involving serious damage to the cutaneous tissue to be treated, that is, anywhere traditional plastering may prove inappropriate or impracticable.

Such devices, usually of complex construction and supplied in varying configurations for adaptation to the most unpredictable of contingent situations, have opposite ends which are fastened to respective undamaged portions of the broken bone, using screws firmly set in the bone material of these portions.

Thus, for example in the case of a tibial fracture, the opposite ends of a corresponding (tibial) fixation device are secured across the fractured region. In other cases, where the fracture involves a joint such as an ankle, the bone screws of a corresponding external fixation device are set in the shinbone and the talus.

These bone screws for fastening the external fixation device, and thus ensuring the device effectiveness, generally include a screw head designed for engagement by a suitable driver, and a screw shank having a threaded portion which usually tapers toward a screw tip at the opposite end from said head.

In particular, the screw head is advantageously formed with a flat which extends parallel to the screw axis, milled on one side of the screw shank, for example.

In view of the overall dimensions of an external fixation device of this kind, which dimensions are largely dictated by the complexity of the device construction and functions and by its cantilever mount to the broken bone, as well as of its hindering and interfering character being a source of general "inconvenience" for both the surgical team and the patient, a demand exists in the art for a reduction of the device overall volume to within more acceptable limits.

A way of filling this demand could be, for example, that of using bone screws in different lengths, which would protrude only marginally from the fixation device in their installed condition.

For the purpose, the prior art provides each fixation device with a comprehensive kit of bone screws, all alike as regards design and construction but with different lengths, thereby providing, for application situations selected statistically as being those of most frequent occurrence, screws in suitable lengths which will not protrude out of the fixation device in their installed state, yet be readily accessible.

This prior approach, while being widely employed and satisfactory, is not exhaustive of all the possible situations with which a surgeon may find himself confronted, and is left with certain technical drawbacks, foremost among which is the difficulty of quickly making an unfailing assessment of the appropriate screw length in the field. It is well recognised, in fact, that despite his previous experience, skill and amount of know-how, the surgeon may not always be able to promptly gauge the most appropriate length of a screw to a particular external fixation device and a particular type of setting in a specific spot.

Consequently, in view of that once the setting operation has been started with a selected screw, it becomes most inconvenient if not impossible to discontinue the operation in order to have that screw replaced with a more suitable one, it is not infrequent for one or more bone screws to be left to protrude undesirably out of the external fixation device at the end of a setting operation, and become a likely cause of trouble.

Another drawback is the wide selection of screws that must be made available to cover the largest possible number of surgical cases. This increases the uncertainty of the choice, on the one side, and aggravates the equipment cost due to such screws.

U.S. Pat. No. 4,790,297 discloses a method and system for fixing one or more levels of the vertebrae of a spinal column. In this system cannulated wires are provided for being inserted over guide wires through rigid plates into the vertebrae for securing the plates to the vertebrae.

The heads of such screws are much thicker than their respective shanks and are divided into an upper and a lower portion by a slot. Once the screw has been fixed to the bone, this slot allows the upper portion of the head to be separated from the remainder of the screw by twisting the upper portion.

Due to the large heads and to the presence of a plate, the screws according to U.S. Pat. No. 4,790,297 have a fixed length and therefore display the same inconveniences as those of the above-cited prior art screws.

The underlying technical problem of this invention is to provide bone screws with such structural and functional features as to overcome the aforementioned drawbacks of the prior art.

SUMMARY OF THE INVENTION

The concept behind this invention is to provide a screw having a head substantially as thick as the shank with at least first and second flats, aligned to each other near the screw head and separated by a non-flat portion. The non-flat portion is advantageously formed with an annular groove.

Based on this concept, the technical problem is solved, according to this invention, by a bone screw for securing external fixation devices to broken bones which has the features set forth in claim 1 and following.

The features and advantages of a bone screw according to the invention will be apparent from the following description of an embodiment thereof, to be read in conjunction with the accompanying non-limiting drawings.

BRIEF DESCRIPTION OF THE DRAWINGS

In the drawings:

FIG. 1 is a perspective view of a bone screw according to the invention;

FIG. 2 is a plan view of the screw in FIG. 1;

FIG. 3 is a sectional view taken along line III—III in FIG. 2;

FIG. 4 shows in plan view a modified embodiment of the inventive screw;

FIG. 5 is an enlarged view showing schematically a detail of the screw in FIG. 4.

DETAILED DESCRIPTION

Referring to the drawing views, generally shown at 1 is a bone screw according to the invention intended for securing external fixation devices (not shown) as used to reduce bone fractures.

The screw 1 comprises a cylindrical shank 2 which has a longitudinal axis, indicated at X-X in FIG. 2, a head indicated generally at 3 and formed at the free end 4 of the shank 2, and a threaded portion 5 which is terminated with a tip 6 opposite from said free end 4.

The screw head 3, which has substantially the same thickness as the shank 2, includes a first rectangular flat 7 which extends parallel to the axis X-X from said free end 4. The flat 7 is formed on one side of the shank 2, e.g. by a milling process.

A second rectangular flat 8 is formed aligned and parallel to the first flat 7 at a spacing therefrom.

Defined between said flats 7, 8 is a non-flat portion 9 which will be referred to as the "spacer portion" hereinafter and throughout the appended claims.

Advantageously, the flats 7, 8 are preferably the same size.

However, in a modified embodiment shown in FIG. 4, a screw 10 is provided with the first flat 7 longer than the second flat 8.

Either flats 7, 8 define respective shoulders 7a, 8a on the shank 2, as are required for proper engagement of the bone screw by a driver (T-wrench), not shown because conventional.

By way of illustration, the screw 1 may be 175 mm in overall length, including a threaded portion 5, itself 60 mm long.

Different lengths may be provided for the surgeon to have a variety of bone screws available according to necessity. For example, screws may be suitable provided in overall lengths of 140 mm, including a threaded portion 5 of 40 mm; 210 mm including a 70 mm threaded portion; or 255 mm, including a threaded portion of at least 80 mm.

Where the screw is 175 mm long, a preferred shank 2 diameter would be 6 mm, with the outside diameter of the threaded portion 5 being the same size at the shank 2. At the tip end 6, the outside diameter of the threaded portion would be 4 mm.

The operation can be regarded to have been carried out successfully, as far as the bulk volume of the whole external fixation device is concerned, when the set bone screw 1 of this invention has its first flat 7 fully embedded in the fixation device or only slightly standing above its surface. If, on the contrary, said first flat 7 protrudes from the fixation device too much or to an unacceptable extent, the shank can advantageously be cut off at the spacer portion 9, i.e. between the flats 7 and 8, thereby reducing substantially the bulk represented by the first flat 7 portion with no forfeiture of the capability to release the screw 1 (screw it off intentionally) by application of the T-wrench to the second flat 8.

Advantageously, to facilitate the above shank cutting operation, the spacer portion 9 is formed with a groove 11 of a predetermined depth which effectively weakens the shank 2 to a predetermined extent.

Preferably, the groove 11 is an annular groove, but it could extend through a shorter arc and be C-shaped in cross-section, for example.

A preferred diameter of the spacer portion at the groove 11 is 4 mm.

It should be noted that said groove 11, additionally to defining the location on the non-flat portion 9 where the shank 2 is to be cut off, if necessary, effectively weakens the shank at that location, such that the application of an excessively high torque will result in the screw head being snapped off locally.

Thus, the invention does solve the technical problem, in that it provides a universal type of bone screw and reduces the need to maintain a range of different length screws.

Furthermore, the stress raiser provided by the separating groove in the spacer portion has an important advantage in that it eliminates the risk of the screw breaking, while being driven in, at different locations with respect to the free end represented by the screw head.

What is claimed is:

1. A bone screw for use with external fixation devices in the reduction of bone fractures comprising a screw body having a substantially cylindrical shank (2) with a longitudinal axis (X-X), a head (3) formed at a free end (4) of said shank (2) and having substantially the same thickness as the shank (2), and a single threaded portion (5) terminating with a tip (6) at an end opposite said free end (4) and having a diameter no greater than the diameter of said shank (2); said head (3) including a first flat (7) extending parallel to said longitudinal axis (X-X) from said free end (4); a second flat (8) in said screw body aligned with said first flat (7) at a predetermined spacing therefrom; and an annular non-threaded spacer portion extending between said flats (7,8) having a longitudinal length sized to receive the fixation device and for enabling said screw body to be cut off at a location within said spacer portion for reducing the overall longitudinal length of the screw body.

2. A bone screw according to claim 1, in which said spacer portion (9) is formed with a groove (11) of predetermined depth for defining a cutting off location.

3. A bone screw according to claim 2, in which said groove (11) is annular in shape.

4. A bone screw according to claim 3, in which a bottom of said groove has a diameter of 4 mm.

5. A bone screw according to claim 1, in which said flats (7,8) are rectangular in shape.

6. A bone screw according to claim 1, in which said flats (7,8) are identical with each other.

* * * * *